United States Patent [19]

Thalmeier et al.

[11] Patent Number: 5,658,761
[45] Date of Patent: Aug. 19, 1997

[54] STROMAL CELL LINES FROM HUMAN BONE MARROW AND THEIR USE

[75] Inventors: Karin Thalmeier, München; Peter Dörmer, Gilching, both of Germany

[73] Assignee: Gsf-Forschungszentrum für Umwelt und Gesundheit GmbH, OberscheleiBheim, Germany

[21] Appl. No.: 584,425

[22] Filed: Jan. 11, 1996

Related U.S. Application Data

[63] Continuation-in-part of PCT/EP94/02224, Jul. 7, 1994.

[30] Foreign Application Priority Data

Jul. 7, 1993 [DE] Germany .................... 43 22 570.5

[51] Int. Cl.$^6$ .................... C12N 5/10; C12N 15/66
[52] U.S. Cl. ............ 435/69.4; 435/69.51; 435/69.52; 435/172.1; 435/172.3; 435/372; 435/373
[58] Field of Search .................... 435/69.1, 69.4, 435/69.51, 240.2, 69.52, 240.21, 240.23, 172.3, 320.1, 172.1

[56] References Cited

PUBLICATIONS

Chambers et al., "Generation of osteoclast-inductive and osteoclastogenic cell lines from the H-2KBTSA58 transgenic mouse", *Proceedings of the National Academy of Sciences*, vol. 90, pp. 5578–5582, Jun. 1993.

Cicuttini et al., "Support of human cord blood progenitor cells on human stromal cell lines transformed by SV40 large T antigen under the influence of an inducible (metallothionein) promoter", *Blood*, vol. 80, No. 1, pp. 102–112 (1992).

Cohen et al., "Critical spatial requirement within the origin of Simian Virus 40 DNA replication", *Journal of Virology*, vol. 51, pp. 91–96 (1984).

Fields et al., *Virology*, second edition, 1990, Raven Press, New York, USA, pp. 1593–1607.

Gualtieri et al., "Hematopoietic regulatory factors produced in long-term murine bone marrow cultures and the effect of in vitro irradiation", *Blood*, vol. 64, No. 2, pp. 516–525 (1984).

Harigaya et al., "Generation of functional clonal cell lines from human bone marrow stroma", *Proceedings of the National Academy of Sciences*, vol. 82, pp. 3477–3480 (1985).

Singer et al., "Simian Virus 40-transformed adherent cells from human long-term marrow cultures: cloned cell lines produce cells with stromal and hematopoietic characteristics", *Blood*, vol. 70, pp. 464–474 (1987).

Thalmeier et al., "Establishment of two permanent human bone marrow stromal cell lines with long-term post irradiation feeder capacity", *Blood*, vol. 83, No. 7, pp. 1799–1807 (1994).

Thalmeier et al., "Establishment and characterization of human bone marrow stromal cell lines", *International Society for Experimental Hematology*, XXIst Annual Meeting, Jul. 1992, Providence, Rhode Island, USA (cited in Experimental Hematology, vol. 20, No. 6, p. 815, Jul. 1992).

Williams et al., "Generation of murine stromal cell lines supporting hematopoietic stem cell proliferation by use of recombinant retrovirus vectors encoding SV-40 large T antigen", File Server STN Karlsruhe, File Biosis Abstract No. 88:460575 *Mol. Cell. Biol.* 8 (9), pp. 3864–3871 (1988).

Patent Abstracts of Japan, vol. 10, No. 67 (C–333), 15 Mar. 1986.

*Primary Examiner*—James Ketter
*Attorney, Agent, or Firm*—Nikaido, Marmelstein, Murray & Oram

[57] ABSTRACT

A human bone marrow stromal cell line, which is characterized in that the cells of the cell line, after irradiation which results in the growth being arrested, remain adherent, is suitable for use as a feeder layer for supporting the proliferation of blood cells.

19 Claims, 7 Drawing Sheets

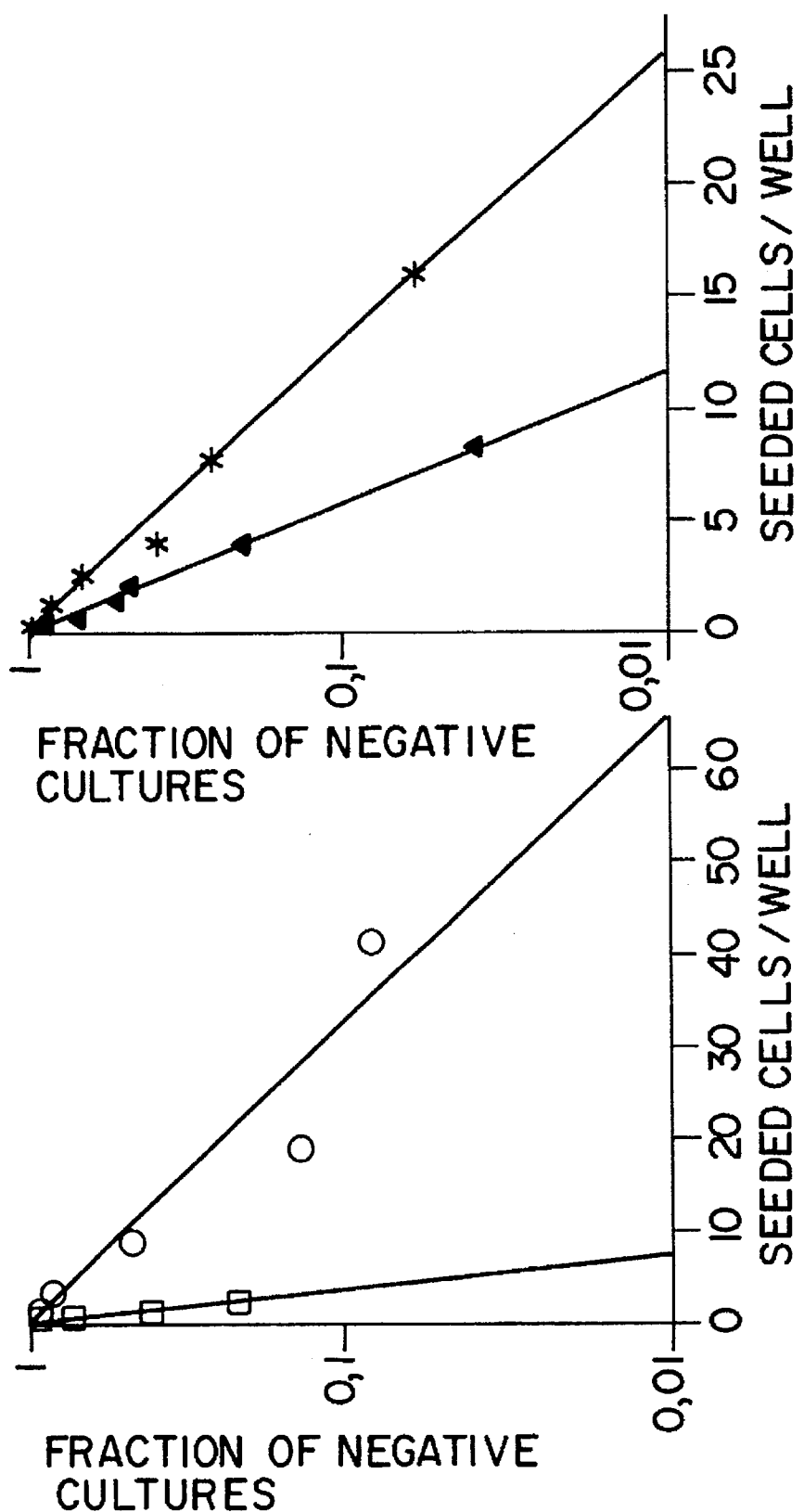

STROMAL CELL LINES FROM HUMAN BONE MARROW AND THEIR USE

CROSS REFERENCE TO RELATED APPLICATION

This application is a continuation-in-part of International Application PCT/EP94/02224, filed Jul. 7, 1994, and designating the U.S.

FIELD OF THE INVENTION

The present invention is directed to new stromal cell lines which are characterized in that they persist adherent following ionizing-irradiation at doses up to, and exceeding 20 Gy for growth arresting. This renders them particularly useful as feeder cells, supporting the long-term proliferation of feeder layer dependent cells.

BACKGROUND OF THE INVENTION

Maintenance and differentiation of hemopoietic progenitor and stem cells in long-term bone marrow culture (LTBMC) critically depends on the presence of a functional layer of adherent stromal cells [1–6]. The precise role of stromal cells in hemopoiesis has not yet been fully elucidated. Stromal cells, however, are an important source of mediators required for the controlled differentiation and proliferation of progenitor cells [7–9]. In addition stromal cells also provide a complex functional extracellular matrix supporting direct cell-to-cell contacts between stromal and progenitor cells. The heterogeneous cellular composition of this stromal layer including macrophages, fibroblasts, adipocytes and endothelial cells [1–3], makes it extremly difficult to analyze the role of each cell type in hemopoietic development.

Established bone marrow stromal cell lines provide a useful tool for the analysis of discrete stromal functions. While a number of spontaneously immortalized murine stromal cell lines have been described [13–15] attempts to establish corresponding human lines have failed [16]. Human bone marrow stromal cell lines are also described in K. Thalmeier et al. [41]. However, no cell lines which remain adherent after irradiation are described in this publication.

Some of the problems associated with the establishment of human stromal cell lines have been solved by introducting DNA into the cellular genome encoding the SV40 large T-Ag [17–21]. This has been accomplished by a variety of gene transfer methods including Ca-phosphate precipitation [17], electroporation of recombinant SV40 constructs [18, 20, 21], and infection with SV40 wild-type viruses [19, 20]. These stromal cell lines have been used as model systems for analyzing stromal cell-progenitor cell interactions [22–26]. Nevertheless the use of SV40-immortalized stromal cell lines as supportive feeder layers in LTBMCs still has two important drawbacks. Firstly, SV40-immortalized cells grow very rapidly for up to 100 cell generations [27] and then enter a characteristic crisis leading to the death of the cells [19]. Secondly, growth of SV40-immortalized stromal cells cannot be inhibited by irradiation or mitomycin C without detachment from the culture flasks [21].

In this invention there are described new human bone marrow stromal cell lines and their use. These cell lines proliferate at a high rate and can be growth-arrested by irradiation without detachment. The functional capacity of the cell lines according to the invention as feeder cells is exemplified by their ability to support the long-term proliferation of e.g. CD34$^+$ enriched human cord blood progenitor cells and clonogenic growth of the feeder-dependent cell line BL70.

SUMMARY OF THE INVENTION

The invention provides stromal cell lines from human bone marrow which are characterized in that the cells of the cell line stay adherent after irradiation in such a manner that the cell lines are arrested in growth.

The invention further provides a method of production of a growth inhibited adherent stromal cell line from human bone marrow and the use of said stromal cell line as feeder layer for the cultivation of blood cells.

This invention provides stromal cell lines from human bone marrow which contain in their genome viral DNA sequences of simian virus 40 (SV 40) which are characterized in that the origin of replication of the SV40 virus is defect. A part of the late SV40 genes which code for the packaging proteins is deleted in a preferred embodiment of the invention.

It is further preferred that the stromal cell line according to the invention contains at least the viral DNA sequences of simian virus 40 which code for the T-antigen.

The invention also includes the stromal cell lines L87/4 (DSM ACC 2055) and L88/5 (DSM ACC 2056) which are deposited at the Deutsche Sammlung von Mikroorganismen und Zellkulturen GmbH, Braunschweig, DE.

Still further this invention provides the use of a stromal cell line according to the invention as feeder layer for blood cells, preferably for hematopoetic cells or precursor cells, e.g. osteoclasts. The invention additional provides the use of the stromal cell lines according to the invention for the production of growth factors/cytokines.

The invention also includes the use of a stromal cell line according to the invention as expression cell line for genes cloned in vectors, said genes replicating under the control of the large T-antigen of SV 40.

BRIEF DESCRIPTION OF THE DRAWINGS

Legends to Figures

FIG. 3 Support of cord-blood GM-CFCs by the stromal cell lines L87/4 and L88/5. Nonadherent cord-blood cells produced on the stromal cell lines L87/4 and L88/5 were harvested weekly following culture week 2 and assayed in methylcellulose cultures for myeloid progenitors. Colonies (>50 cells) were counted 14 days after plating. The results represent two representative and independent experiments.

DETAILED DESCRIPTION OF THE INVENTION

Figure 1A:
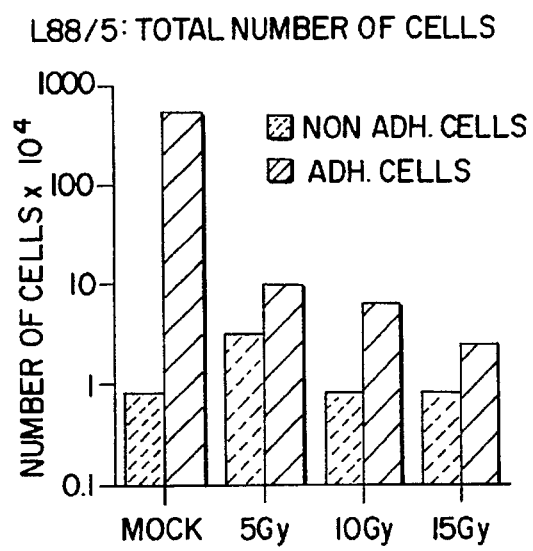
FIG. 1 Radiosensitivity of the stromal cell lines L87/4 and L88/5. Cells were plated at a density of 5×10$^5$/ml in 75 cm$^2$ flasks in LTC medium and irradiated with 5–20 Gy. After irradiation the medium was changed completely and the Sells were incubated for 7 days (37° C., 5% CO$_2$) in LTC medium. On day 8 adherent and non-adherent cell numbers were determined (A, B) and the cells plated in agar containing GCT-CM. Day 14 agar colonies were counted in C and D.
Figure 1B:
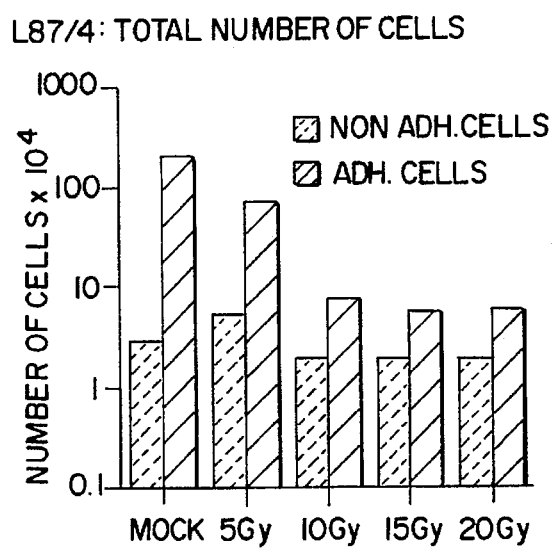
Figure 1C:
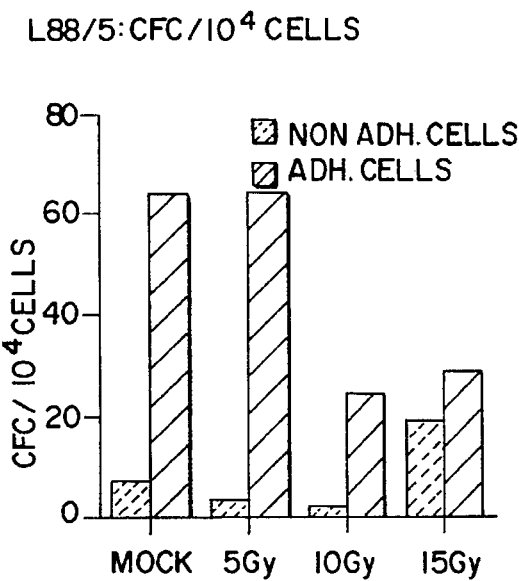
Figure 1D:
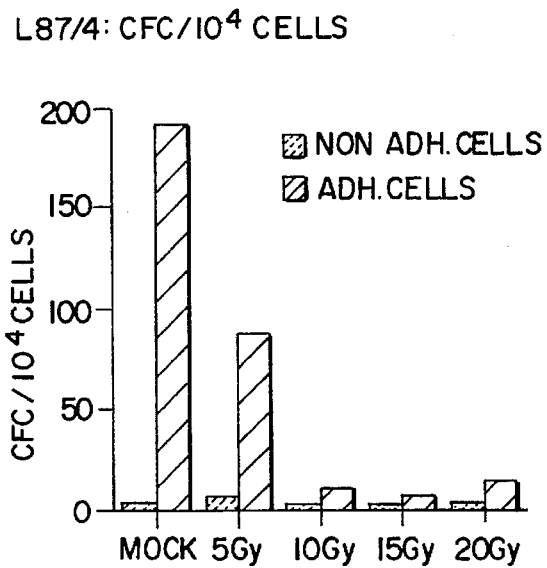

In contrast to all of the human bone marrow stromal cell lines of the state of the art, the cell lines according to the invention offer the following advantages:

a) Homogeneity

As distinct from primary stroma, the cell lines consist of an exactly defined uniform cell population. Thus, experimentation variations occurring when using primary cells from varying probands are excluded;

b) Permanence

Primary stromal cells and most of the SV-40 immortalized cell lines die after a limited number of divisions. The stromal lines as claimed are capable of unlimited division (in terms of "immortalized");

c) Growth Inhibition by Irradiation

For experiments in which the stromal cells are used as a "feeder layer" (=feeder cells) for hematopoietic progenitors, the growth of the stromal cells must be inhibited and at the same time the cells must adhere to the cell culture dish. Heretofore described SV-40 immortalized lines, after being irradiated, separate from their support, whereas the cell lines as claimed stop growing and also remain adherent;

d) Production of Hematopoietic Growth Factors

Feeder cells for hematopoietic precursor cells control the growth and differentiation thereof by, inter alia, production of growth factors. The cell lines as claimed are capable of producing large mounts of these growth factors, wherein factor production can be influenced both by irradiation and stimulation with interleukin-1;

e) Spontaneous changes of the cell lines caused by virus production are excluded.

There may also be used other vectors which contain at least the viral DNA sequences of the Simian virus 40 which codes for the T-antigen and for which the replication origin of the SV40 virus is defect. Vectors in which, additionally, the late genes of the SV40 virus which code for the envelope proteins are deleted are also suitable. Primary adherent cells from human bone marrow were transfected with the help of such SV40 plasmid vector. Transfection was carried out with liposomes. The DNA transfected in the course of the lipofection reaches the nucleus of the bone marrow cells and there integrates into the chromosomal DNA. The site of integration of the vector is not foreseeable here, that is to say, it occurs by chance. The expression of the SV40 T-antigen integrated into the cellular genome brings about immortalization of these cells.

The lines established in this manner are immortalized, exhibit very short doubling times, and form a homogeneous cell population.

The employed vectors pUC 12 and pBR 322 as well as the viral DNA sequences of the Simian virus 40 are commercially available.

The cell lines according to the invention, after irradiation which results in the growth being arrested, remain adherent. In this, the cells continue being viable but they are no longer capable of dividing. They are producing large mounts of hematopoietic growth factors/cytokines.

Irradiation of the stromal cell lines is carried out according to the methods familiar to one skilled in the art, as are described, e.g., in [21]. Usually, ionizing irradiation at 5 to 20 Gray (Gy) is performed. Before irradiating, it is expedient to allow the cells to adhere to the surface of the vessel used (confluency). After irradiation, the surviving cells (more than about 80%) remain adherent. The killed cells detach from the surface and are in this way easy to separate from the cells according to the invention, for example by exchanging the medium.

The adherent cells so obtained are viable for a prolonged period of time so that they are able to support the culturing of feeder layer-dependent cells such as, for instance, hematopoietic progenitor cells or peripheral blood. Typically, after 7 days at least 90% and after two or three weeks at least 50% of the adherent cells will be viable still. As a culture medium (also for co-cultivation with blood cells) there can be applied all culture media known to one skilled in the art as being suitable for stromal cells.

Stromal cells according to the invention are to be understood to mean also the active membrane-containing subcellular fragments thereof which, analogous to the complete cells, promote the proliferation and/or differentiation of blood cells. Such fractions may be subcellular vesicles, for example, which are obtained by hypotonic shock, or cell-free membrane vesicles which can be obtained, for example, by incubation with cytochalasin B. There is also suitable an eluate from the cells according to the invention which can be recovered, for instance, after incubation with sodium chloride and sodium citrate. Such fractions of the cells according to the invention can be further pitied using the methods familiar to one skilled in the art, for instance by chromatographic purification wherein the activity of the fraction (suitability as a feeder layer) must be examined after each purification step.

Membrane vesicles are prepared, for example, according to the method of Maul et al. [38], which is incorporated herein by reference. Another method is described, for example, by Jett et al. [39], which is incorporated herein by reference. After washing the cells in EARL's buffer, glycerol is added to the cells at a final concentration of 30% in three steps at 15-minute-intervals. After centrifugation, lysis is carried out, multiple centrifugation is performed, and the vesicle fraction is enriched. The enriched fractions are examined for their property of supporting the proliferation of blood cells, preferably hematopoietic precursor cells or stem cells.

"Supporting the proliferation of cells" as used in the invention is understood to mean that the cell lines according to the invention support the survival, proliferation, and possibly also the production of blood/growth factors/cytokines by the blood cells. In this, the cells of the cell lines according to the invention are bound adherently to a surface (preferably a culture flask). The feeder layer-dependent cells settle on that feeder layer and are stimulated in growth and/or differentiation. The feeder layer supplies the blood cells with growth factors such as cytokines, and adhesion molecules.

"Supporting the differentiation" especially means supporting the differentiation of cells which are not terminally differentiated (are not at the end of the pathway of differentiation). Examples of such cells are pluripotent stem cells and blood progenitor cells.

By blood cells there are to be understood, for example, hematopoietic stem cells, hematopoietic progenitor cells or peripheral blood cells. Examples are CD34+ human cord-blood progenitor cells or also lympoid cells (model cells are the BL 70 cell lines [35]) as well as stem cells isolated from bone marrow, human umbilical cord-blood or peripheral blood, progenitor cells such as granulocyte, erythroid or megacaryocyte progenitor cells.

Typically, a cell density of $5 \times 10^5$ cells/ml of culture is applied for a surface of 75 cm$^2$.

In a preferred embodiment for culturing feeder layer-dependent cells, the cell lines according to the invention are first of all grown until they reach confluency, and then irradiated. After irradiation, the medium is exchanged and, thereby, the killed and non-adherent cells are also removed. The cells so prepared can be used directly as a feeder layer. However, it is preferred to culture the cells for several hours in a serum-free medium, prior to use.

In a preferred embodiment of the invention, the stromal cells according to the invention can be used for supporting the expansion of hematopoietic stem cells without differentiation. The conditions for such expansion are described in M. R. Koller et al. [40], which is incorporated herein by reference.

Such an expansion of stem cells without differentiation is particularly useful for the proliferation of stem cells which are ex vivo genetically modified by transduction. Such modified stem cells can be used in gene therapy. The transduction can be done according to the state of the art, e.g. by using retroviruses or DNA and liposomes. As the yield of such a transduction is usually very low, expanded transduced stem cells are of great value in ex vivo gene therapy.

For preparing the growth-arrested adherent, immortal, SV40 transformed stromal cells it is preferred to culture the cells until they reach confluency, and to repeatedly passage the stromal layer until the cells enter a growth crisis. This usually occurs after 25 to 30 cycles. Thereafter, the cells which are dividing at a very slow rate only, or which essentially are not dividing at all, are collected, for instance, by trypsinization and replaced in a new culture with fresh medium. These cells are irradiated as described above. The growth-arrested adherent stromal cells remain adherent whereas the irradiation-killed cells are detached and are easy to remove in this manner.

Surprisingly the stromal cell lines according to the invention have been found to produce growth factors to a large extent. This production can be induced by irradiation at varying intensities (preferably between 5 and 20 Gy) and/or by addition of IL-1 (5 to 50 U/ml, preferably 5 to 15 U/ml) and/or dexametasone (0.5 to $2 \times 10^{-6}$ mol/l). Induction by irradiation mainly results in G-CSF production being increased (to about 50 ng/ml of culture, and IL-6 production to about 100 U/ml at as high as 20 Gy). IL-1 stimulates, in addition, GM-CSF production. The growth factors produced in this manner by the cells can be purified according to the methods familiar to one skilled in the art.

In the transfection of the bone marrow cells, the following procedure was carried out:

Bone marrow cells were cultured for 2 to 3 weeks in long-time culture medium (McCoy's 5a supplemented with 12.5% fetal calf serum, 12.5% horse serum, 1% sodium bicarbonate, 1% MEM nonessential amino acid solution, 1% L-glutamine (200 mM), 1% penicillin-streptomycin solution—all solutions from Gibco—$10^{-4}$M α-thioglycerol, $10^{-6}$M hydrocortisone) (5% $CO_2$; 37° C.) until the stromal layer reached subconfluency. One day before transfection, the adherent stromal cells were collected by trypsinization and plated in 25 cm$^2$ culture flasks at a cell density of $5 \times 10^5$ cells/mi. The transfection was carried out with cesium chloride-purified plasmid DNA (psV-IN1 and pUCIN-1 wt).

The transfection was carried out as follows, in accordance with the transfection protocol of the firm Serva (IBF Instruction Sheet No. 2942 10).

The semiconfluent cells were washed once with PBS, once with McCoy's 5a, and incubated for 5 to 18 hours with a freshly prepared plasmid/transfectam mixture in 8 ml serum-free long-time culture medium in 25 cm$^2$ culture flasks. After transfection, the cells were washed twice with PBS/10% FCS and cultured in LTC medium to confluency. The transfected cells were selected by repeated passaging of the stromal layer at a ration of 1:2. After about 25 to 30 passages, the immortalized cells entered a so-called growth crisis. This crisis was overcome in that cells which divided only slowly or did not divide at all were detached from their support by trypsinization and replaced in a new culture flask. Cells treated in this manner recovered spontaneously from the crisis and displayed an immortalized phenotype.

The stromal cell lines L87/4 and L88/5 differ by the following properties:
Expression of the T-antigen
  L87/4: low expression (passage 14)
  L88/5: strong expression (passage 14)
Site of integration of the viral DNA
  different integration sites in the genome
Constitutive factor production
  L88/4: constitutive production of G-CSF and IL-
  L88/5: low constitutive production of G-CSF and IL-6

The production of G-CSF and IL-6 is inducible in both the cell lines by irradiation.

Some important examples for the use of the cell lines are shown below.

The stromal cell lines according to the invention, and preferably, the cell lines L87/4 and L88/5 can be used for all experiments in which cells growing in dependency of a feeder layer are to be cultured. These are all hematopoietic precursor cells and stem cells as well as precursor cells of bone formation (osteoclasts). There also exist positive results for the growth of early feeder-dependent B tumour cells (BL70) on line 88/5 as well as line 87/4.

Apart from the cultivation of normal hematopoietic precursor cells, the cell lines according to the invention, and preferably, the cell lines 87/4 and L88/5, can be used also for analysis of malignant bone marrow cells from leukemic patients (CML, AML, ALL) under the influence of medicaments, which is of special importance in view of the autologous bone marrow transplantation. Experimental variations which heretofore occurred on account of the use of primary feeder cells from varying test persons are to be excluded here.

Apart from being suited as feeder cells, the cell lines according to the invention, and preferably, the cell lines L87/4 and L88/5, can be used as producer lines for a number of growth factors. Here the extremely high constitutive production of G-CSF of the line L87/4 and IL-6 of the line L88/5 respectively may gain importance. There could be shown furthermore a heretofore undefined, highly stimulating activity of L88/5 cells on the cell growth of 7TD1- and NFS60 cells in conditioned medium (=cell culture supernatant).

There is also possible the use as an expression cell line for genes cloned into vectors which replicate under control of the large T-Ag of SV40. As an example, COS cells are referred to here.

The following examples are provided to aid the understanding of the present invention, the hue scope of which is set forth in the appended claims. It is understood that modifications can be made in the procedures set forth without departing from the spirit of the invention.

EXAMPLES

Example 1

Establishment of Permanent Human Bone Marrow Stromal Cell Lines With Long-term Post-irradiation Feeder Capacity a) Material and Methods Bone Marrow Bone marrow cells for long-term culture and transfection experiments were obtained from freshly resected ribs of hematologically normal patients. All specimens were obtained by informed consent and according to protocols approved by institutional ethics committees.

Long-term Culture

Bone marrow cells were isolated from the rib by aspiration in phosphate buffered saline (PBS). They were plated without any further purification step at a density of $2 \times 10^6$ cells/ml in 75 cm² flasks (Nunc) in Dexter-type long-term bone marrow culture medium (LTC medium: McCoy's 5a medium supplemented with 12.5% preselected fetal calf serum (FCS), 12.5% preselected horse serum (HS), 1% sodium bicarbonate, 1% sodium pyruvate, 0.4% MEM non-essential amino acid solution, 0.8% MEM essential amino acid solution, 1% vitamin solution, 1% L-glutamine (200 mM), 1% penicillin-streptomycin solution (all solutions from Gibco), $10^{-4}$M a-thioglycerol, $10^{-6}$M hydrocortisone). Cultures were incubated at 37° C. in a humidified atmosphere at 5% $CO_2$ and fed weekly by half-medium change.

Establishment of Human Bone Marrow Stromal Cell Lines

Bone marrow cells were cultured for 2–3 weeks in LTC-medium until the stromal layers reached subconfluency. Adherent stromal cells were collected by trypsinization and replaced in 25 cm² culture flasks at a density of $5 \times 10^5$ cells/ml. CsCl gradient-purified plasmid vectors pSVIN-1 (origin-defective SV40 genome cloned in pBR322), and pUCIN-1 (origin-defective SV40 genome cloned in pUG12, late genes partially deleted) were used for the transfection experiments. Transfection using liposomes was carried out essentially as described in the producer's (Serva, Heidelberg) transfection protocol. Briefly, semiconfluent adherent cells were washed once with PBS, once with McCoy's 5a, and incubated for 5 to 18 hours with a freshly prepared plasmid/transfectam mixture in 8 ml serum-free LTC medium in 25 cm² flasks. After transfection cells were washed twice with PBS/10% FCS and cultured in 10 ml LTC medium to confluency. After a latency period of about 6 weeks transfected cells started overgrowing primary stromal cells and were passaged continuously at a ratio of 1:2. Transfected cells were maintained in LTC medium at 37° C. in a humidity incubator at 5% $CO_2$.

Southern Blot Experiments

After at least 6 cell passages DNA of transfected cells was purified by CsCl gradient centrifugation [28], digested with selected enzymes, and electrophoresed on a 0.8% agarose gel. DNA was blotted on Hybond N filters (Amersham Buchler, Braunschweig) and hybridized with a radioactively labeled BamHI/pSVIN-1 fragment encoding SV40 large T-Antigen.

Northern Blot Experiments

Total RNA of transfected cells was isolated by the guanidinium-isothiocyanate extraction method [29], glycoxylated and fractionated on a 1% agarose gel (20 µg per slot). RNA was blotted on Hybond N filters (Amersham Buchler, Braunschweig) and hybridized with a radioactively labeled BamHI fragment of the plasmid pSVIN-1 coding for the SV40 large T-Ag.

Radiosensitivity Assay

Transfected cells were plated at a density of $5 \times 10^5$/ml in 75 cm² flasks in LTC medium and grown for 18 hours. Subsequently they were irradiated with 5–20 Gy using a cesium-137 gamma ray source (Atomic Energy of Canada, Ontario, Canada). After irradiation the medium was changed completely and the cells were incubated for 7 days (37° C., 5% $CO_2$) in LTC medium. On day 8 adherent and non-adherent cells were harvested by trypsinization, cell numbers were counted, and the colony-forming potential of the irradiated cells was measured by counting day 14 colonies in agar.

Colony-forming Assay

To examine the clonogenic potential of transformed stromal cell lines adherent cells were harvested by trypsinization (0.25% trypsin, Gibco) and plated in semi-solid agar cultures as reported [30]. In brief, stromal cells were plated in triplicate at a concentration of $1 \times 10^5$ cells/ml using equal mounts of 0.6% Bactoagar (Difco, Detroit, Mich.) and double-strength Iscove's modified Dulbecco's medium (IMDME; Gibco) containing 40% preselected FCS. Colony growth was stimulated by 10% (vol/vol) giant cell tumor-conditioned medium (GCT-CM; American Type Culture Collection, Rockville, Md.). Cultures were incubated for 14 days at 37° C. in a humified atmosphere and 5% $CO_2$ in air. Fibroblast colonies were scored on day 14 using an inverted microscope (32-fold magnification).

Immunofluorescence Staining for Phenotyping (Table 1)

a) Indirect Immunofluorescence Staining

L88/5 and L87/4 cells were cultured on glass slides washed with calcium-free PBS (PBSd) and fixed for 10 min in a 1:1 mixture of ice-cold methanol and acetone. After rinsing the slides with PBSd diluted rabbit antiserum against Factor VIII-related antigen (Behring; 100 µl antiserum+1.5 ml PBSd) was layered on the slides. The slides were then incubated at 37° C. for 30 minutes in a humidity chamber, rinsed with PBSd, and overlaid with a FITC-labeled secondary anti-rabbit antibody. After incubation at 37° C. for 30 minutes the slides were washed with PBSd, overlaid with a mixture of glycerol and PBSd (1:1) and covered with a coverslip.

b) Immunofluorescence Staining for FACS Analysis

Adherent stromal cells were detached from the culture flask by incubation with collagenase (0.1 U/ml)/dispase (0.8 U/ml) for 15 min at 37° C. Cells were washed with PBSd, suspended in IF-buffer (PBSd with 0.1% sodium acid and 2% FCS), and labeled for 30 min at 4° C. with the first antibody which was either FITC-conjugated, PE-conjugated or unlabeled. Cells were then washed twice with 1 ml IF-buffer, and in the case of unlabeled first antibody treated as described above with a second FITC- or PE- labeled antibody. Stained cells were suspended in 1 ml IF-buffer and analyzed by a FACScan flow cytometer (Becton Dickinson).

Cytochemical Staining for Phenotyping (Table 1)

Cells were cultured on glass slides washed with PBSd air-dried and stained with chloracetate-esterase or α-naphthylesterase as described by the producer's instructions. (Sigma).

Limiting Dilution

Adherent feeder cells were seeded in 96 well plates, grown to confluency and irradiated (MRC5, 50 Gy; BM feeder, 50 Gy; L88/5, 15 Cry; L87/4, 20 Gy) in a Cs137 source (Atomic Energy of Canada, LTD). After 24 hours, BL70 cells were washed twice in serum-free medium and added at the indicated cell densities in at least 24 well plates. Plates were fed twice weekly, and outgrowth of colonies was monitored up to day 40. All limiting dilution experiments were performed in RPMI1640 supplemented with 5% FCS, 2 mM L-glutamine and antibiotics. BL70 cells were kept in the same medium in the presence of irradiated (50 Gy) MRC5 cells. MRC5 cells were cultured in Dulbeccos MEM supplemented with 10% FCS, 2 mM L-glutamine and antibiotics.

Coculture Experiments with $CD34^+$ Enriched Human Cord-blood Cells

Percoll-separated mononuclear cord-blood cells were either stained with anti-CD34 monoclonal antibody (Dianova, Hamburg) directly conjugated to fluorescein isothiocyanate (FITC) and then sorted on a FACStarPlus (BD FACS Systems; Becton Dickinson) for high CD34 expression or the CD34 positive cells were isolated by using Dynabeads M-450 directly coated with the mAb BI-3C5 [34].

$CD34^+$ cord-blood cells were plated in 24 well plates ($5 \times 10^3$ cord-blood cells/well) on irradiated semiconfluent L87/4 (20 Gy) and L88/5 (15 Gy) stromal cells in LTC medium. Cultures were maintained at 37° C. for 5 weeks with half medium changes weekly following culture week 2. Non-adherent cells were assayed in semisolid medium for the presence of erythroid (BFU-E) and myeloid (GM-CFC) progenitor cells. Cultures were plated with $10^4$ non-adherent cells/ml in IMDM, 30% FCS, 1% BSA, $10^{-4}$M α-thioglycerol, 5% PHA-LCM, 0.98% methyl cellulose, 3 U/ml EPO—all substances from the Terry Fox Laboratories—and 100 ng/ml kit-Ligand. Cultures were plated in 1 ml volumes in 35 mm tissue culture plates in 5% $CO_2$ at 37° C. and colonies were counted on day 14.

b) Establishment and Characteristics of Early Passage Human Bone Marrow Stromal Cell Lines BM cells of a 70-year-old hematologically normal male patient were cultured in 25 $cm^2$ flasks in conventional Dexter-type LTBMC for 3 weeks. Confluent stromal layers were passaged once and transfected with either pSV-IN1 or pUG-IN1 plasmid vectors by lipofection. Both plasmids contain the sequences coding for the SV40 T-antigen known to be a transforming factor [31,32]. Ten passageable cell lines were selected by their growth advantage over primary stroma were obtained after lipofection. Spontaneous outgrowth of non-adherent EBV-immortalized B cells was observed in 20% of the culture flasks.

Five of the 10 cell lines designated L87/4, L88/5, L90/7, L91/8 and L87/12 were selected for further studies. All cell lines display fibroblastoid morphology, harbour a stably integrated SV40 construct and express SV40 large T-Ag as determined by Northern blotting (data not shown). The integration site of the plasmid vector is different in each cell line. Three of the 5 cell lines were clonal after six passages while 2 were oligoclonal. The SV40 transformed cell lines grew at a comparatively high rate for 25 to 30 cell passages and then entered a crisis. Two of the 5 lines were rescued subsequently (lines L88/5 and L87/4). They have now been maintained in continuous culture for more than 70 passages (18 months). All further experiments were performed with clonal postcrisis L88/5 and L87/4 cell lines.

Several parameters including site of SV40 integration, SV40 T-Ag expression, CD68 expression in L87/4 and response to irradiation are stably maintained in pre- and post-crisis cells. In post-crisis cells they are stable for more than 30 passages. The cell lines according to the invention can be maintained as adherent growth-arrested cell layers after irradiation with doses of up to 20 Gy. It is noteworthy that even higher doses of ionizing radiation are tolerated, if these cells are recharged in time with CD34-enriched umbilical cord-blood cells at low densities.

Figures 1, 3A:
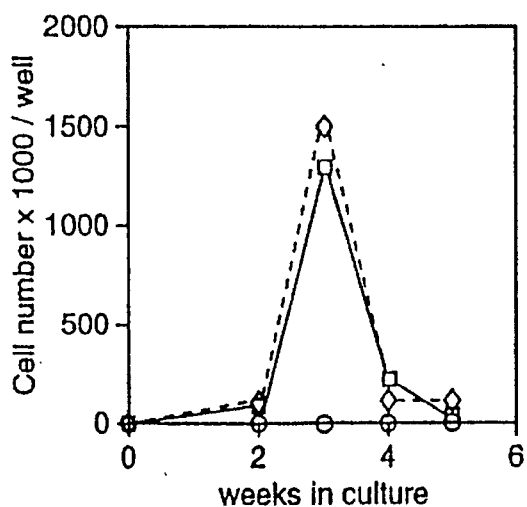
Figures 2, 3A:
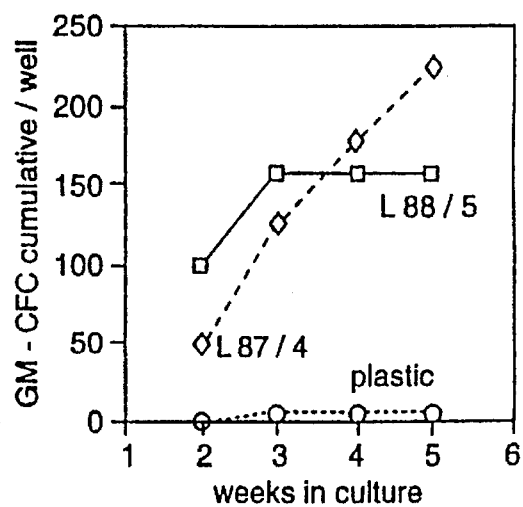
FIG. 2 Limiting dilution analysis of response of BL70 cells to different feeder cells. BL70 cells were seeded under limiting dilution conditions in the presence of (A) L87/4 cells (circles) or L88/5 cells (boxes). Statistical evaluation revealed a frequency of f=13.5 in the presence of L87/4 cells (r=−0.951; y$_o$=0.925) and f=1.5 in the presence of L88/5 cells (r=−0.990; y$_o$=1.04). For comparison, (B) shows limiting dilution analysis of BL70 cells seeded in the presence of MRC5 cells (asterisks; b=5.7; r=−0.996; y$_o$=1.00) or primary bone marrow stroma (triangles; f=2.5; r=−0.996; y$_o$=0.98).
Figures 1, 3B:
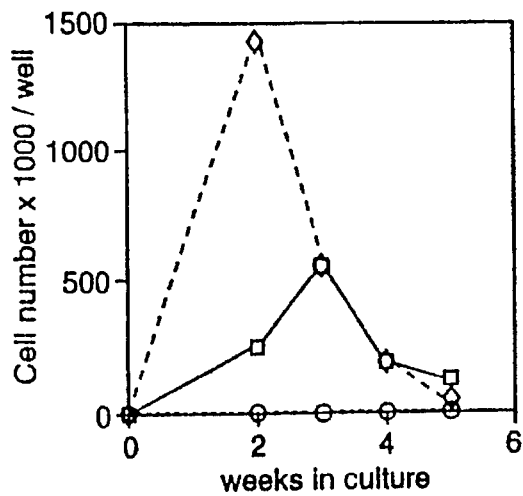
Figures 2, 3B:
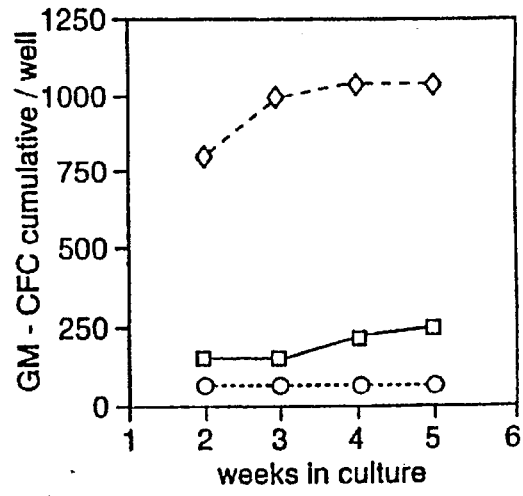

In a preferred embodiment of the invention the cell lines show expression of CD10 and CD13 and non-expression of hemopoietic markers (see Table 2). Especially preferred are cell lines which express the macrophage marker CD68. FIG. 2 illustrates characteristic phenotypes of the cell lines according to the invention.

Figure 6:
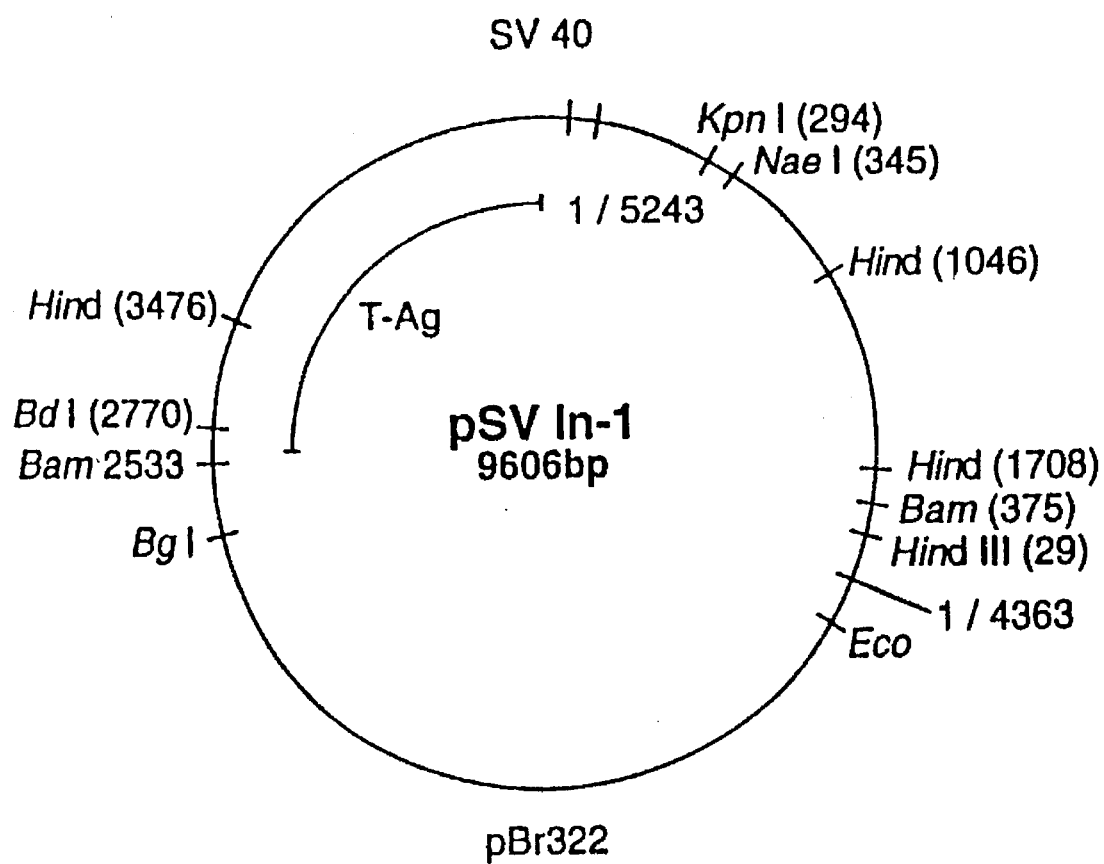
FIG. 6 shows an employed transfection vector (psV IN-1) as is known from Cohen et al., J. Virol. 51 (1984) 91–96.
Figure 7:
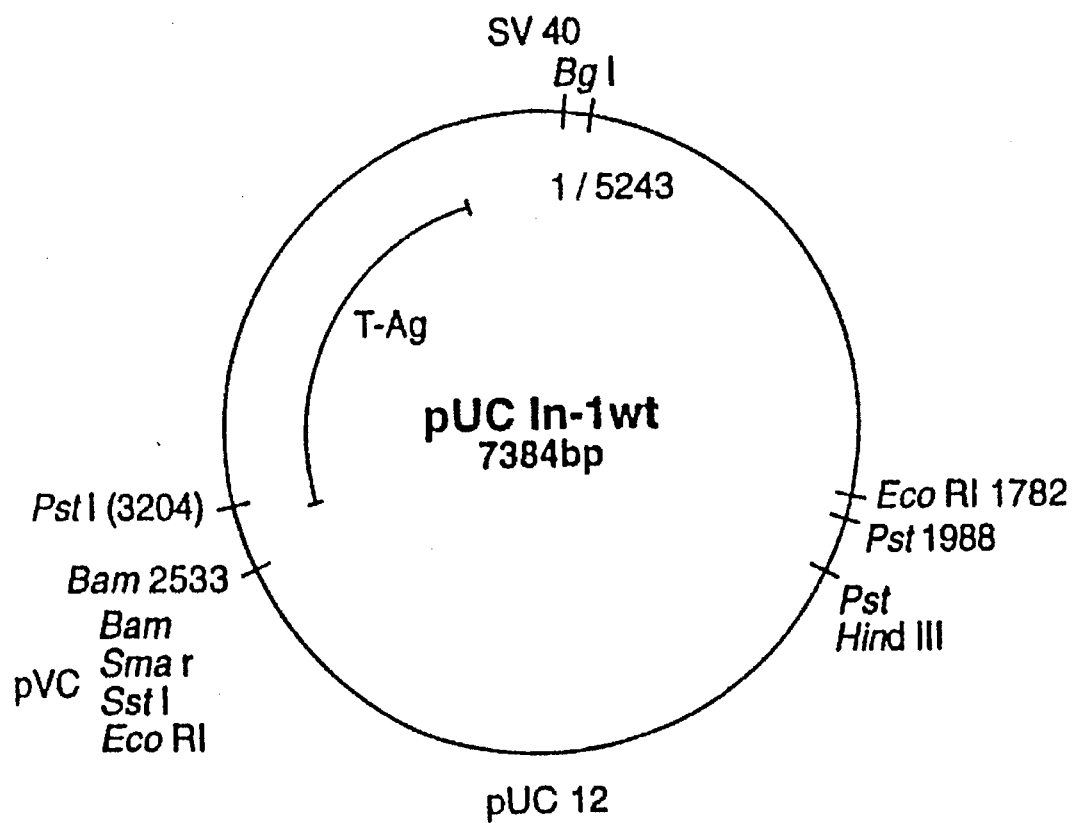
FIG. 7 shows a second vector derivable therefrom (pUC IN-1 wt). Here SV40-DNA was cut from pSVIN-1 at the cleavage sites Bam/Pst and the nucleotide sequences of bp 1988–2533 were removed. Then the deleted SV40-DNA was cloned into the pUC 12 Bam/Pst cleavage site.

The cell lines according to the invention also possess feeder capacity in post-crisis passages (e.g. passage 60). This is demonstrated by their ability to maintain clonogenic cell proliferation of stroma cell dependent BL cell lines (e.g. BL70) for more than 5 weeks. The BL70 assay clearly demonstrates that the cell lines produce all factors necessary for malignant B cell proliferation. This does not preclude the possibility that they produce further cytokines supporting the growth and differentiation of other cell types as well. As shown by PCR analysis cell lines according to the invention produce a variety of hemopoietic growth factors including IL-6, IL-7, IL-8, IL-10, IL-11, KL, LIF, G-CSF, GM-CSF and M-CSF. This cytokine profile shows that the cell lines according to the invention are capable of supporting long-term culture of normal primary hemopoietic progenitor cells, for example the development of GM-CFCs (FIG. 6) and BFU-Es from $CD34^+$ enriched cord-blood cell cultures.

Characterization of the Stromal Cell Lines L88/5 and L87/4

By phase contrast morphology both stromal post-crisis cell lines exhibit fibroblastoid morphology. Cells divide rapidly with doubling times of one day for L88/5 and two days for L87/4. The cells show contact inhibition and do not form foci in liquid culture. They grow into fibroblastoid colonies when plated in semi-solid agar in the presence of 1% GCT-CM.

Both cell lines are positive for SV40 T-antigen expression and display the same genomic SV40 integration sites as previously observed in the pre-crisis L87/4 and L88/5 cells. As shown by immunofluorescence, L87/4 and L88/5 express the stromal cell surface markers CD10 and CD13 while they do not express a variety of hemopoietic cell markers (Table I). Nevertheless L87/4 can be distinguished from L88/5 by expressing the macrophage marker CD68.

Radiosensitivity of L88/5 and L87/4 Cells

Figure 4A:
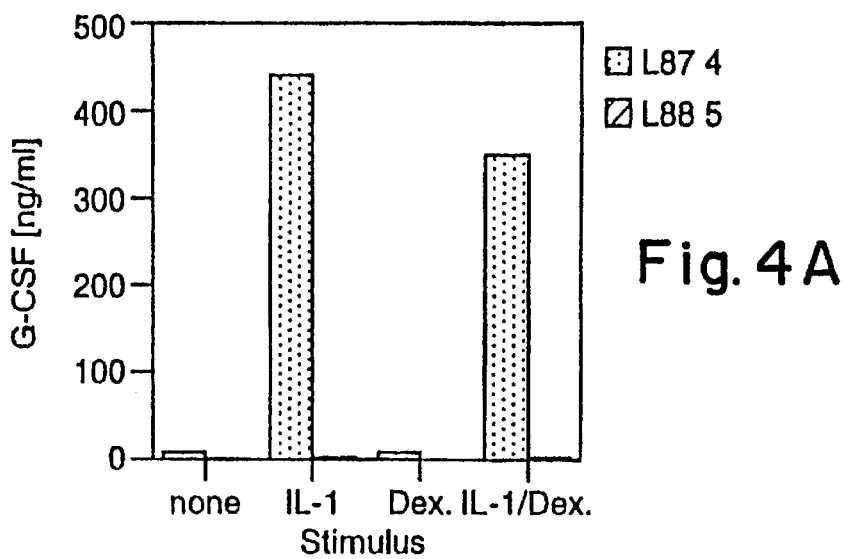
FIG. 4 G-CSF, IL-6, and GM-CSF secretion of IL-1α and/or Dexamethasone treated L87/4 and L88/5 cells. Cells were incubated for 24 hrs in LTC medium without hydrocortisone or in LTC medium supplemented with either IL-1α (10 U/ml) or dexamethasone ($10^{-6}$M) or both. supernatants were tested for IL-6 activity with the 7TD1 and G-CSF activity with the NFS60 indicator cell line by MTT-test. GM-CSF activity in the supernatants was measured by RIA.
Figure 4B:
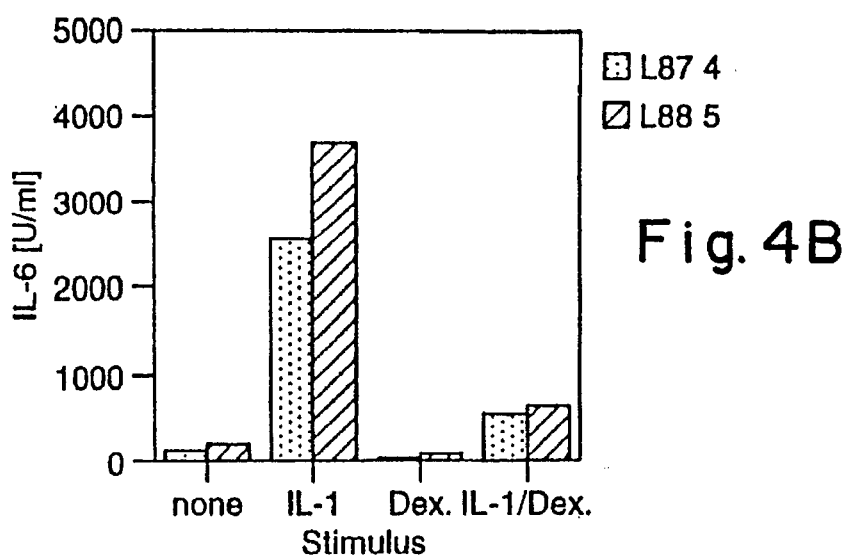
Figure 4C:
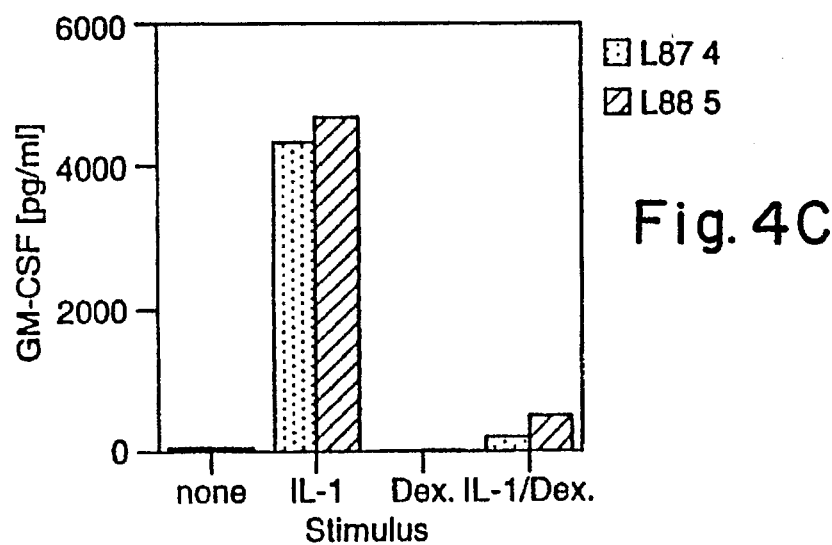

L88/5 and L87/4 cells were cultivated and irradiated as indicated in FIG. 4 and described in Material and Methods. Both cell lines can be irradiated with up to 15 Gy without detachment. Proliferation and colony formation of L88/5 ceases at doses exceeding 15 Gy while L87/4 cells retain their ability to grow and form colonies in soft agar. L87/4 must be irradiated with 20 Gy to abolish proliferation in suspension culture and clonal growth in soft agar (FIG. 1).

Cell line L87/4 can be irradiated at even higher doses without cell detachment if irradiated cell layers are recharged within 24 hours with low numbers ($5 \times 10^3$/ml) of CD34-positive umbilical cord-blood cells.

L88/5 and L87/4 Cells Substitute for Fibroblast and BM Feeder Cells

Figure 5A:
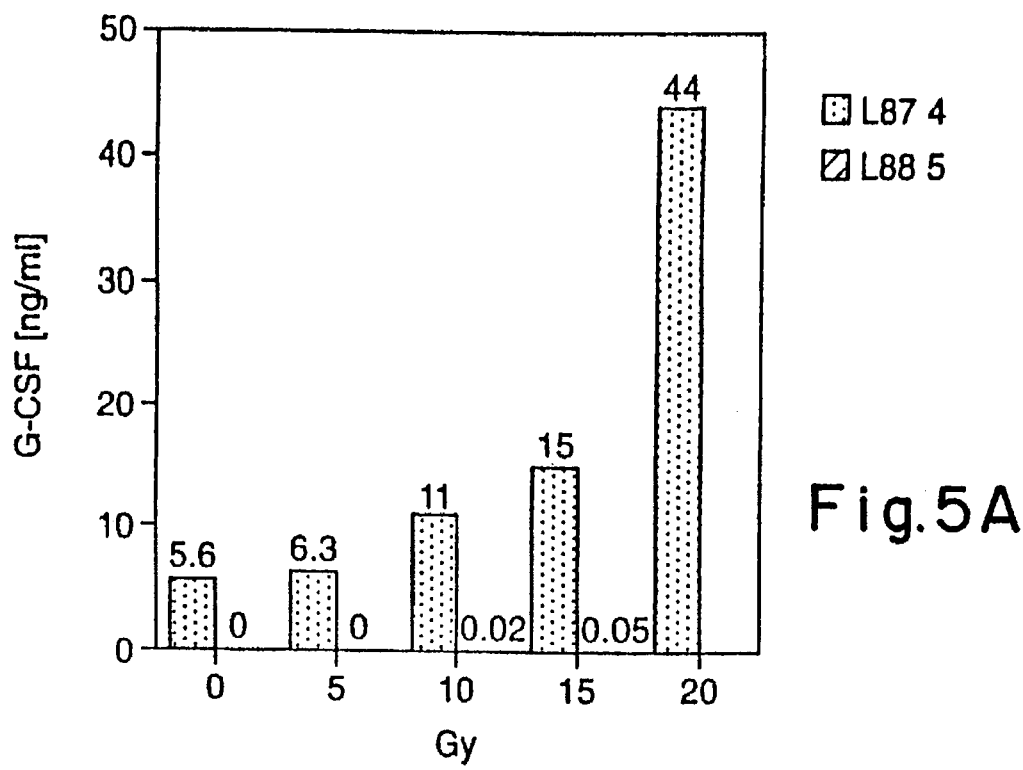
FIG. 5 G-CSF and IL-6 secretion of irradiated L87/4 and L88/5 cell lines. Cells were grown to subconfluency in LTC medium and irradiated with 0–20 Gy. After irradiation the medium was changed completely, cell supernatants were harvested after 24 hrs of incubation and tested for IL-6 activity (7TD1) and G-CSF activity (NFS60) by MTT-test.
Figure 5B:
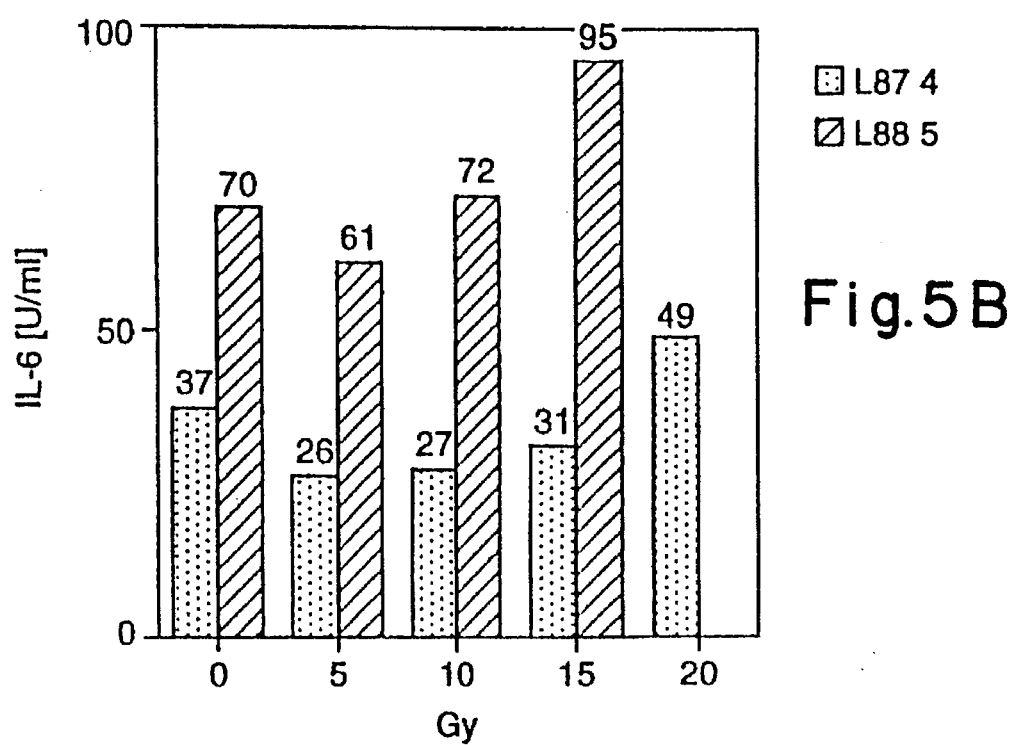

A number of Burkitt lymphoma (BL) cell lines depends on a feeder layer of irradiated human fibroblasts if grown at low cell densities under low serum conditions. At high cell densities they do not require feeder cell layers. Feeder function in this system can be provided by a series of primary human and rodent fibroblast cells. However several available, SV40-immortalized human fibroblast cell lines constantly failed to support the proliferation of a model BL line, BL70 [35]. As shown in FIG. 2, irradiated (15 Gy) L88/5 cells as well as irradiated (20 G) L87/4 cells support the clonogenic growth of BL70 cells even better than primary irradiated bone marrow stromal cells and human MRC5 fibroblasts. BL70 cells dying within 2 days in the absence of feeder cells can be maintained on irradiated L87/4 and L88/5 feeder layers for more than 5 weeks. The graphical representation of BL70 limiting dilution assays (FIG. 5) indicates a single hit kinetic. This demonstrates that L88/5 cells and L87/4 cells (as well as MRC5 cells or primary BM stroma) provide all factors necessary for optimum proliferation of BL70 cells.

L87/4 and L88/5 Cells Support Long-term Hematopoiesis of Human Cord-blood Progenitors Semiconfluent irradiated L87/4 (20Gy) and L88/5 (15 Gy) cells seeded in 24 well plates were charged with CD34$^+$ human cord-blood cells ($5 \times 10^3$ CD34$^+$ cells/well) and cultured for 5 weeks in LTC medium. Up to culture week 5 both stromal layers supported the proliferation of non-adherent cord-blood cells with a maximum of cell numbers observable two to three weeks after initiation of the cultures. The number of non-adherent cells is amplified about 200 fold during the culture period compared to the number of input cord-blood cells. Large numbers of myeloid (GM-CFC, FIG. 3) and erythroid (BFU-E) progenitor derived colonies were present in the non-adherent cell fraction up to five weeks after culture initiation as determined by methyl cellulose colony formation assays.

TABLE 1

Phenotypes of the post-crisis stromal cell lines L87/4 and L88/5

|  | L87/4 | L88/5 |
|---|---|---|
| c-kit | − | − |
| HLA-DR | − | − |
| CD11a, CD11b, CD14, CD23, CD32, CD33, CD34, CD36, CD38, CD56, CD61, CD64 | − | − |
| CD10 | + | ++ |

TABLE 1-continued

Phenotypes of the post-crisis stromal cell lines L87/4 and L88/5

|  | L87/4 | L88/5 |
|---|---|---|
| CD13 | +++ | +++ |
| CD68 | + | − |
| CD71 | +++ | ++ |
| Factor VIII related antigen | − | − |
| Chloracetate esterase | − | − |
| α-naphtylesterase | − | − |
| SV40 T-Ag | +++ | +++ |
| Smooth muscle type Actin | − | − |
| Laminin | − | − |
| Fibronectin | +++ | +++ |
| Vitronectin | +++ | +++ |

Example 2

Constitutive and Modulated Cytokine Expression in Cell Lines According to the Invention Cell Culture A series of cell lines and primary cells were used as positive controls for RNA analysis. There were: U937 cells (ATCC: CRL1593; human histiocytic lymphoma), HL60 cells (ATCC: CCL240; human promyelocytic leukemia), K562 cells (ATCC: CCL243; human CML), MelJuso (gift by Dr. Johnson, Department of Immunology; LMU-Munich), and 5637 cells (ATCC: HTB9; human bladder carcinoma) were grown in RPMI 1640/10% FCS in a humidity incubator (37° C.; 5% $CO_2$). All cell lines were subcultured twice weekly.

To culture activated T cells peripheral blood mononuclear cells of healthy volunteers were separated by a Percoll gradient and incubated in IMDM/10% FCS supplemented with phytohemagglutinine (1 vol. %) and phorbol 12-myristate 13-acetate (10 ng/ml). After incubation for 8 hours the cells were harvested and RNA was prepared by the guanidinium-isothyocyanate extraction method [31].

Primary stromal layers were established as described in example 1.

Exposure of L87/4 and L88/5 Cells to IL-1α and Dexamethasone

L87/4 (passage 96) and L88/5 (passage 98) cells were plated at densities of $2 \times 10^5$ cells/ml in 25 cm$^2$ culture flasks (Nunc) and incubated for 24 hours in LTC medium. The medium was removed completely and replaced by fresh LTC medium without hydrocortisone or by LTC medium supplemented with either IL-1α (10 U/ml) or dexamethasone ($10^{-6}$M), or both. Cells were then incubated for another 24 hours (37° C.; 5% $CO_2$) before RNA was extracted. Culture supernatants were collected for cytokine bioassays and RIAs.

Quantification of Stromal Cytokine Release by Bioassays

Crude conditioned medium of stromal cells (L87/4; L88/5) was tested for its proliferation-enhancing activity in MTT assays as described [36]. 7TD1 cells were used to assay IL-6 production. G-CSF activity was measured by a highly responsive NFS60 subline. The specifities of cell line responses were checked by adding appropriate neutralizing antibodies.

Quantification of Stromal Cytokine Release by RIAs

Crude conditioned medium of L87/4 and L88/5 cells was tested for IL-1β and GM-CSF concentrations as described elsewhere [37].

In conclusion, it is shown that two permanent stromal cell lines according to the invention (e.g. L87/4 and L88/5) produce an array of cytokines thought to contribute to the maintenance of human hemopoietic progenitors this pattern of cytokine production is being partly augmented and partly suppressed due to irradiation and glucocorticoids (FIGS. 4 und 5).

Expansion of Hematopoietic Progenitor/Stem Cells

For preparing the growth-arrested stromal cells from the cell lines, cells are preferably plated at $2\times10^5$/mL in 25-cm$^2$ culture flask (for stationary culture) or in 25 cm$^2$ bioreactor culture flasks (for continuous perfusion culture). After 24 hrs of growth in long-term culture (LTC) medium, cells are irradiated preferably with 15 Gy for L88/5, and 20 Gy for L87/4. Within 24 hrs thereafter the medium is exchanged completely, thus also removing the detached stromal cells. Concomitantly, stroma cell-depleted (2 hrs plastic adherence) normal or genetically modified mononuclear cells (MNC) from bone marrow ($10^6$/mL) or MNC from umbilical cord blood ($10^6$/mL) or CD34+ enriched peripheral blood stem cells ($10^4$/mL) are added in a total volume of 10 mL of LTC medium without addition of cytokines. After a further 24 hrs period for settlement of the immature progenitors to the stromal cells, medium circulation is started in the continuous flow experiments (20 mL/day) using a peristaltic pump. Long-term culture at 37° C. is continued for 2–3 weeks with 20% oxygen and 5% $CO_2$ supply.

REFERENCES

1. Dexter T. M.: Stromal cell associated haemopoiesis. J Cell Physiol 1:87, 1982 (suppl)
2. Allen T. D., Dexter T. M.: The essential cells of the hemopoietic microenvironment. Exp Hematol 12:517, 1984
3. Dexter T. M., Allen T. D., Lajtha L. G.: Conditions controlling the proliferation of haemopoietic stem cells in vitro. J Cell Physiol 91:335, 1977
4. Gartner S., Kaplan H. S.: Long-term culture of human bone marrow cells. Proc Natl Acad Sci USA 77:4756, 1980
5. Hocking W. G., Golde D. W.: Long-term human bone marrow cultures. Blood 56:117, 1980
6. Toogood I. R. G., Dexter T. M., Allen T. D., Suda T., Lajtha L. G.: The development of a liquid culture system for the growth of human bone marrow. Leuk Res 4:449, 1980
7. Kaushansky K., Lin N., Adamson J. W.: Interleukin 1 stimulates fibroblasts to synthesize granulocyte-macrophage and granulocyte colony-stimulating factors. J Clin Invest 81:92, 1988
8. Fibbe W. E., van Damme J., Bilau A., Goselink H. M., Voogt P. J., van Eeden G., Ralph P., Altrock B. W., Falkenburg J. H. F.: Interleukin-1 induced human marrow stromal cells in long-term marrow culture to produce granulocyte colony-stimulating factor and macrophage colony-stimulating factor. Blood 71:430, 1988
9. Lee M., Segal G. M., Bagby G. C. J.: Interleukin 1 induces human bone marrow-derived fibroblasts to produce multilineage hematopoietic growth factors. Exp Hematol 15:983, 1987
10. Bentley S. A.: Bone marrow connective tissue and the hematopoietic microenvironment. Br J Haematol 50:1–6, 1982
11. Verfaillie C., Blakolmer K., McGlare P.: Purified primitive human hematopoietic progenitor cells with long-term in vitro repopulating capacity adhere selectively to irradiated bone marrow stroma. J Exp Med 172:509–520, 1990
12. Liesveld J. L., Winslow J. M., Kempski M. C., Ryan D. H., Brennan J. K., Abboud C. N.: Adhesive interactions of normal and leukemic human CB34+ myeloid progenitors: Role of marrow stromal, fibroblast and cytomatrix components. Exp Hematol 19:63–70, 1991
13. Hunt P., Robertson D., Weiss D., Rennick D., Lee F., Witte O. N.: A single bone marrow-derived stromal cell type supports the in vitro growth of early lymphoid and myeloid cells. Cell 48:997, 1987
14. Quesenberry P., Song Z., McGratz E., McNiece I., Shadduck R., Waheed A., Baber G., Kleeman E., Kaiser D.: Multilineage synergistic activity produced by a murine adherent marrow cell line. Blood 69:827, 1987
15. Collins L. S., Dorshkind K.: A stromal cell line from myeloid long-term bone marrow cultures can support myelopoiesis and lymphopoiesis. J Immunol 138:1082, 1987
16. Lanotte M., Allen T. D., Dexter T. M.: Histochemical and ultrastructural characteristics of a cell line from human bone marrow stroma. J Cell Sci 50:281, 1981
17. Harigaya K., Handa H.: Generation of functional clonal cell lines from human bone marrow stroma. Proc Natl Acad Sci USA 82:3477, 1985
18. Novotny J. R., Duehrsen U., Welch K., Layton J. E., Cebon J. S., Boyd A. W.: Cloned stromal cell lines derived from human Whitlock/Wittetype long-term bone marrow cultures. Exp Hematol 18:775, 1990
19. Singer J. W., Charbord P., Keating A., Nemunaitis J., Raugi G., Wight T. N., Lopez J. A., Roth G. J., Dow L. W., Fialkow P. J.: Simian virus 40-transformed adherent cells from human long-term marrow cultures: Cloned cell lines produce cells with stromal and hematopoietic characteristics. Blood 70:64, 1987
20. Aizawa S., Yaguchi M., Nakano M., Inokuchi S., Handa H., Toyama K.: Establishment of a variety of human bone marrow stromal cell lines by the recombinant SV40-adenovirus vector. J Cell Physiol 148:245–251, 1991
21. Ciuttini F. M., Martin M., Salvaris E., Ashman L., Begley C. G., Novotny J., Maher D., Boyd A. W.: Support of human cord blood progenitor cells on human stromal cell lines transformed by SV40 large T-antigen under the influence of an inducible (metallothionein) promoter. Blood 80:102–112, 1992
22. Yang Y.-C., Tsai S., Wong G. G., Clark S. C.: Interleukin-1 regulation of hematopoietic growth factor production by human stromal fibroblasts. J Cell Physiol 134:292–296, 1988
23. Kohama T., Handa H., Harigaya K.-i.: A burst-promoting activity derived from the human bone marrow stromal cell line KM-102 is identical to the granulocyte-macrophage colony-stimulating factor. Exp Hematol 16:603–608, 1988
24. Nemunaitis J., Andrews D. F., Crittenden C., Kaushansky K., Singer J. W.: Response of simian virus 40 (SV40)-transformed, cultured human marrow stromal cells to hematopoietic growth factors. J Clin Invest 83:593–601, 1989
25. Nemunaitis J., Andrews D. F., Mochizaki D. Y., Lilly M. B., Singer J. W.: Human marrow stromal cells: Response to interleukin-6 (IL-6) and control of IL-6 expression. Blood 74:1929–1935, 1989
26. Slack J. L., Nemunaitis J, Andrews III D. F., Singer J. W.: Regulation of cytokine and growth factor gene expression in human bone marrow stromal cells transformed with simian virus 40. Blood 75:23 19–2327, 1990
27. Neufeld D. S., Ripley S., Henderson A., Ozer H.: Immortalization of human fibroblasts transformed by origin-defective simian virus 40. Molecular Biology 7 (8):2794–2802, 1987
28. Sambrook I., Fritsch E. F., Maniatis T.: Molecular cloning. A laboratory manual. Cold Spring Harbor Laboratory Press, 1989
29. Chirgwin J., Przybala A., Mac Donald R., Rutter W.: Isolation of biologically active ribonucleic acid from sources enriched in ribonuclease. Biochemistry 18:5294–5299, 1979
30. Mergenthaler H.-G., Brühl P., Dörmer P.: Kinetics of myeloid progenitor cells in human micro long-term bone marrow cultures. Exp Hematol 16:145–149, 1988
31. Kuhar S., Lehman J. M.: T-antigen and p53 in pre- and postcrisis simian virus 40 transformed human cell lines. Oncogene 6:1499–1506, 1991
32. Chang S.-E.: In vitro transformation of human epithelial cells. Biochim Biophys Acta 823 (3):161–194, 1986
33. Andrews III D.-F., Lilly B.-M., Tompkins K.-C., Singer W.-J.: Sodium vanadate, a tyrosine phosphatase inhibitor, affects expression of hematopoietic growth factors and extracellular matrix RNAs in SV40 transformed human marrow stromal cells. Exp Hematol 20:449–453, 1992
34. Smeland E. S., Funderud S., Kvalheim G., Gaudernack G., Rasmussen A.-M., Rusten L., Wang M. Y., Tindle R. W., Blomhoff H. K., Egeland T.: Isolation and characterization of human hemotopoietic progenitor cells: An effective method for positive selection of CD34+ cells. Leukemia 6:845–852, 1992
35. Falk M. H., Hültner L., Milner A., Gregory C. D., Bornkamm G. W.: Irradiated fibroblasts protect Burkitt Lymphoma cells from apoptosis by a mechanism independent of BCL-2. Int. J. Cancer, in press (1993)
36. Mosman T.: Rapid colorimetric assay for cellular growth and survival: Application to proliferation and cytotoxity assays. J Immunol Methods 65:55–63, 1983
37. Mortensen B. T., Schifter S., Pedersen L. B., Jensen A. N., Hovgaard D., Nissen N. I.: Development and application of a sensitive radioimmunoassay for human granulocyte-macrophage colony-stimulating factor able to measure normal concentrations in blood. Exp Hematol 21:1366–1370, 1993
38. Maul et al., Technics Insomatic Cell Genetics (1982), Et. J. W. Shay, Plenum Press, New York
39. Jett et al., J. Biol. Chem. 252 (1977) 2134–2142
40. M. R. Koller et al., Large-scale expansion of human stem and progenitor cells from bone marrow mononuclear cells in continuous perfusion culture; Blood, Vol. 82 (2) (1993) 378–384
41. K. Thalmeier et al., Establishment and characterization of human bone marrow stromal cell lines; Exp. Hematology 20 (1992) 815

We claim:

1. A human bone marrow stromal cell line, wherein said cells remain adherent after irradiation which results in the arrest of cell growth and wherein said human bone marrow stromal cell line expresses SV40 large T antigen.

2. The stromal cell line according to claim 1, wherein said cells produce G-CSF and IL-6 after induction by stimulation with interleukin-1, dexamethasone or a combination of interleukin-1 and dexamethasone.

3. The stromal cell line according to claim 1, wherein said cells produce G-CSF and IL-6 after irradiation-induced growth arrest.

4. The stromal cell line according to claim 1, wherein the cells are present as a feeder layer and support the proliferation, differentiation or proliferation and differentiation of blood cells.

5. The stromal cell line according to claim 1, wherein said cells contain viral DNA sequences of simian virus 40, wherein the origin of replication of the simian virus 40 is defective.

6. The stromal cell line according to claim 5, wherein a part of the late simian virus 40 genes which codes for the packaging proteins is deleted.

7. The stromal cell line according to claim 1, wherein said cells contain a stably integrated SV40 construct and express SV40 large T-Ag.

8. A stromal cell line selected from the group consisting of L87/4 and L88/5.

9. A process for the production of growth-arrested, immortal adherent stromal cells from human bone marrow, comprising the steps of
transfecting the cells of a stromal cell line with SV40,
culturing the cells on a support until said cells reach confluency, to produce a stromal layer,
repeatedly passaging the stromal layer until the cells enter a growth crisis,
removing any cells which are dividing at a very slow rate, or are not dividing at all,
removing said stromal layer from said support,
placing said stromal layer in a new culture, and
arresting the growth of said stromal layer by irradiation.

10. The process according to claim 9, wherein said stromal layer is removed from said support by trypsinization.

11. Growth arrested, adherent stromal cells which stimulate the proliferation, differentiation or proliferation and differentiation of blood cells in a cell culture when used as a feeder layer, wherein at least 50% of said cells can be maintained in a culture for two weeks, and wherein the growth of said stromal cells is arrested by irradiation.

12. The growth arrested, adherent stromal cells according to claim 11, wherein growth of said cells cannot be reinstated by the addition of zinc ions.

13. A process for culturing feeder layer-dependent cells comprising co-cultivation of said cells with growth-arrested adherent stromal cells which stimulate the proliferation, differentiation or proliferation and differentiation of blood cells in a cell culture, wherein said stromal cells can be maintained in a culture for two weeks with at least 50% viability, and wherein the growth of said stromal cells is arrested by irradiation.

14. The process according to claim 13, wherein the growth of said stromal cells is arrested by irradiation.

15. A process for producing hematopoietic growth factors, comprising
co-culturing hematopoietic cells or precursor cells with growth arrested, adherent stromal cells which stimulate the proliferation, differentiation or proliferation and differentiation of said hematopoietic cells or precursor cells, and
isolating said hematopoietic growth factors from the resulting cell culture,
wherein said stromal cells contain SV40 DNA sequences in which the origin of replication of the SV40 virus is defective, wherein said stromal cells can be maintained in a culture for two weeks with at least 50% viability, and wherein the growth of said stromal cells is arrested by irradiation.

16. The process according to claim 15, further comprising the addition of interleukin-1, dexamethasone or a combination of interleukin-1 and dexamethasone to support the production of hematopoietic growth factors.

17. The process according to claim 16, wherein said. IL-1 is present in an amount between 5–50 U/ml.

18. The process according to claim 16, wherein said dexamethasone is present in an amount between 0.5 to $2 \times 10^{-6}$ mol/l.

19. A process for the expansion of hematopoietic stem cells which are genetically modified, comprising co-culturing hematopoietic stem cells with growth arrested, adherent stromal cells wherein said stromal cells contain SV40 DNA sequences in which the origin of replication of the SV40 virus is defective, wherein said stromal cells can be maintained in a culture for two weeks with at least 50% viability, and wherein the growth of said stromal cells is arrested by irradiation.

* * * * *